(12) United States Patent
Lennon

(10) Patent No.: US 11,369,536 B2
(45) Date of Patent: Jun. 28, 2022

(54) COMPACT TREATMENT, EXAMINATION AND WAITING STATION

(71) Applicant: HKS, Inc., Dallas, TX (US)

(72) Inventor: James Albert Lennon, Del Mar, CA (US)

(73) Assignee: HKS, Inc., Dallas, TX (US)

( * ) Notice: Subject to any disclaimer, the term of this patent is extended or adjusted under 35 U.S.C. 154(b) by 0 days.

(21) Appl. No.: 17/153,531

(22) Filed: Jan. 20, 2021

(65) Prior Publication Data

US 2021/0361504 A1  Nov. 25, 2021

Related U.S. Application Data

(60) Provisional application No. 62/976,924, filed on Feb. 14, 2020.

(51) Int. Cl.
*A61G 10/00* (2006.01)
*A61B 5/00* (2006.01)

(52) U.S. Cl.
CPC ............ *A61G 10/00* (2013.01); *A61B 5/0046* (2013.01); *A61B 5/4836* (2013.01); *A61G 2200/34* (2013.01); *A61G 2210/50* (2013.01)

(58) Field of Classification Search
CPC ...... A61G 10/00; A61G 10/005; A61G 10/02; A61B 5/0046; A61B 5/4836; A16G 2200/34
See application file for complete search history.

(56) References Cited

U.S. PATENT DOCUMENTS

| 5,308,158 A | 5/1994 | Volgelgessang |
| 6,577,738 B2 | 6/2003 | Norris |

(Continued)

FOREIGN PATENT DOCUMENTS

| CN | 201906129 U | 7/2011 |
| DE | 102016107254 A1 | 10/2016 |
| WO | 20170172933 A1 | 10/2017 |

OTHER PUBLICATIONS

Maney, Kevin, "Sound Technology Turns the Way You Hear On Its Ear", USA Today, May 20, 2003, www.woodynorris.com/Articles/USAToday2.htm, San Diego, CA, USA.

(Continued)

*Primary Examiner* — Carrie R Dorna
(74) *Attorney, Agent, or Firm* — Monty L Ross PLLC; Monty L. Ross

(57) ABSTRACT

A device that adapts/upgrades an existing, or new medical facility to provide a method of examining and treating occupants in a safe, efficient manner which is one quarter the size of conventional examination and treatment spaces through the use of a system that utilizes a modular frame and compartments to organize medical utilities, services and equipment to be more space efficient than conventional examination and treatment spaces. The frame and compartments have a shaped surface that focuses acoustic energy to increase intelligibility between a caregiver and the occupant and at the same time reduce ambient acoustic energy propagation. Additionally, the device can be disassembled, moved and reassembled easily. Further, the surface over the compartments creates a safety barrier between expensive and delicate utilities that mitigates tampering, accidental damage and reduces the possibility of infectious disease transmission.

17 Claims, 6 Drawing Sheets

(56) References Cited

U.S. PATENT DOCUMENTS

| | | |
|---|---|---|
| 7,298,853 B2 | 11/2007 | Norris |
| 2009/0203329 A1 | 8/2009 | White |
| 2011/0199317 A1* | 8/2011 | Kim .................. G06F 3/041 |
| | | 345/173 |
| 2018/0188561 A1 | 7/2018 | Wang |

OTHER PUBLICATIONS

Sadick, Barbara, "ER Cubicles Allow Hosptials To Use Their Limited Space More Wisely", The Wall Street Journal, Apr. 30, 2019, vol. CCLXXIII, No. 100, Journal Report Health Care, New York, NY, USA.

* cited by examiner

COMPACT TREATMENT, EXAMINATION AND WAITING STATION

CROSS-REFERENCES TO RELATED APPLICATIONS

Not Applicable

STATEMENT REGARDING FEDERAL SPONSORED RESEARCH OR DEVELOPMENT

Not Applicable

MOCROFICHE APPENDIX

Not Applicable

BACKGROUND OF THE INVENTION

Field of Invention

This invention relates to providing required medical treatment, supplies and services to occupants requiring examination, treatment, or observation in a highly space efficient, safe, flexible and private environment.

Medical care is expensive and can be inaccessible, involving long waits. It is important to note that medical care is at the vertex of policy changes, technology change and financial pressures, all of which conspire to require successful medical facilities to adapt, change and respond quickly to be viable in a rapidly changing environment. Access to medical care is a function of provider availability, occupant's ability to pay, proper diagnostic tools and the appropriate quantity of examination/treatment spaces to examine and treat the patients. In many cases, the lack of proper waiting, examination and treatment spaces retards the access to care. This is particularly true with emergency care, where long waits are clearly associated with a paucity of waiting, exam and treatment areas. Additionally, space in medical facilities is expensive to construct and hence inherently limited. However, in emergency departments for example, 50% of incoming occupants do not need to be in a large expensive private room on a stretcher, those occupants are referred to as 'vertical' because they could be seated in a chair as opposed to being in a private room on a stretcher ('horizontal'). Yet, there is no research documenting the needs of vertical occupants in a detailed way, except this invention.

Currently, vertical occupants (in emergency care settings) are housed in a waiting room on a chair and escorted to exam, treatment and diagnostic functions when interactions with medical providers is required. Not only does this require an intensity of staff interaction, but also requires a multiplicity of large treatment and examination spaces specifically tailored to each interaction. After a great deal of study of these occupants, what is needed is a carefully designed, compact, safe space to provide privacy along with access to all of the supplies, services and diagnostics necessary to appropriately manage the care of those occupants. After years of study, spaces that are significantly smaller than conventional examination/treatment rooms can provide all of the functions of conventional exam/treatment rooms in one quarter the floor area. While the previous discussion uses the needs of emergency care as an example, a plurality of other medical settings can benefit from a compact, safe and private treatment environment, such as, but not limited to: infusion, surgical recovery, outpatient clinics, freestanding urgent care clinics, freestanding emergency care centers, micro hospitals, industrial medicine in the workplace and clinics served by telemedicine to name a few. The disclosed device allows medical facilities to increase the number of patients that can be treated per square foot, which allows, more patients to be seen at one time, hence reducing waiting times. It also allows medical facilities to build more space efficient treatment areas, thus reducing health care costs. And since this disclosure is equivalent to two treatment/exam areas per one conventional exam/treatment space it is possible to retrofit existing facilities on a 2 to 1 basis very easily. Conventional exam/treatment rooms are built of studs, gypsum board and ceiling components that disallow them from being moved as one unit, or disassembled into components. The disclosed device, as opposed to conventional exam/treatment spaces, has an integral frame that supports the entire assembly and allows it to be easily moved as one unit, or disassembled into components for easy relocation and reassembly in another location within the medical facility.

DESCRIPTION OF PRIOR ART

There are no known devices that allow for the integration/retrofitting/upgrading of medical facilities to provide compact, safe, private treatment areas that allow for the distribution of hospital services to occupants. Three disclosures: U.S. Pat. No. 7,818,840, priority date Oct. 26, 2010. Barnett; Peter Andrew (Costa Mesa, Calif.), Kneale; Todd Douglas (Brea, Calif.), Alexander; Steven Bruce (Rolling Hills Estates, Calif.), Domae; Terrance Paul (Cerritos, Calif.). U.S. Pat. No. 5,991,947, priority date Mar. 2, 1995 Gregory C. Levin; Craig A. Young, U.S. Pat. No. 5,918,331, priority date Aug. 5, 1994 David Hall; John Charles; Grant-Thomas all three of which disclose methods of constructing a mobile trauma treatment platform (which can be best thought of as an enhanced stretcher) that has medical services integrally designing into the stretcher and the stretcher is intended to serve as the means of transport of trauma occupants between a remote injury site (battlefield) and a hospital at which point the occupant would be transferred to a hospital bed. In the disclosures, the method of connection to utilities is to only be used with specially constructed treatment platforms, in mobile units which are part of their disclosures, and are not treatment platforms in a hospital. In all of the previous disclosures none are suitable to be used in conventional hospitals, outpatient clinics or industrial medical sites.

BRIEF SUMMARY OF THE PRESENT INVENTION

The present invention comprises a frame that can be attached to a conventional hospital, outpatient facility, or industrial medicine site wall structure that supports a series of modular compartments that house medical services, power and occupant amenities to be close to the occupant and mounted at optimal positions for medical staff access. The invention includes a novel design of modular compartments that are attached to the frame which allows for sound reduction and has doors over hospital services that both protects the occupants from hospital born infections (nosocomial infections) and the staff from having to secure sensitive services from occupant tampering. It should be noted that the disclosed device locates all of the necessary medical services and supplies, in the optimum position for staff utilization, but requires one quarter the space of a typical examination/treatment room. That characteristic allows hospitals and other medical facilities utilizing this device to see double the occupants in the same space as typical exam/treatment rooms, while having all of the capability to treat occupants.

Additionally, the frame and compartments are easily relocatable to other parts of a facility to quickly and inexpensively change their clinical environment to respond to changes in policy, technology and provider characteristics. The frame and modular compartments are designed to connect to wall outlets to convey medical utilities, power and communication between a supply source of the utilities and the invention. Occupants in medical facilities often need medical services such as pressurized oxygen, suction, treated natural air, power, EKG monitoring, communication and other devices which the frame and compartments organize for efficient treatment of the occupant. These utilities in conventional exam/treatment space are mounted on the wall either behind the occupant or extending through a column structurally mounted to the ceiling. In conventional exam/treatment spaces, the outlets for the utilities are in inconvenient locations to be accessed by caregivers and are the subject of accidental disconnection during routine procedures. Further, during life threatening events caregivers must enter into combat with the tubes and cables extending between the utility outlets on the wall and the occupant.

The present invention moves the utility outlet connection points to a series of modular compartments that have doors (which may be power or manually actuated) to deliver a plurality of utilities including but not limited to EKG, vacuum, oxygen, medical air, exam lights, gloves, commonly used medical supplies (such as bandages, tongue depressors, etc), trash containers which are located in a position that will not be accidentally disconnected or disturb emergency or routine procedures. Further, the shape of the compartments provides a novel method of focusing sound to attenuate occupant speech between adjacent occupants and to amplify speech between a caregiver and the occupant. Sidewall dividers between occupants, in the preferred configuration, would be piezo electric glass to allow for occupant privacy in which the sidewalls are select-ably opaque or clear depending on the electrical status of the glass which can be controlled by a switch on the sidewall. Other configurations may have solid side walls, or no sidewall at all. In the preferred configuration, two poles are located on either side of the open side of the frame that will act to support the frame vertically and provide mounting points for equipment (I. V. pumps, computer terminal support arms) and future devised equipment.

The frame has modular positions for utilities, supplies, services and occupant amenities thus allowing the frame to support, in the preferred configuration, 9 compartments for utilities, supplies, occupant belongings and trash along with other supplies needed by the utilities. Additionally, on a side wall to the occupant are controls for lights, nurse call, 110v power, USB power, distraction/education devices (such as TV, Internet) along with a pull-down shelf for occupant belongings are provided in the preferred configuration. Other configurations may have varying numbers of services and utilities depending on the mission of the device (outpatient clinic, industrial medicine, infusion, etc.). And other configurations allow for any device, such as, but not limited to, IV pump, occupant communication devices, or any device or utility now known or future devised that conforms to the dimensional and connection constraints of the frame. All 9 positions on the frame have the ability to be moved allowing for relocation of services and utilities to be in the appropriate position for the given occupant use. The frame has the ability to be connected to additional frames allowing for a series of frames to be efficiently placed in a space. Such arrangements include, in the preferred configuration, side by side in a linear arrangement, offset from one another and radial configurations to fit into irregular spaces. Further, the minimum size is 5' wide by 7'6'" deep, but the frame can be expanded to adjust to any dimension from 5' wide to 8' wide by 7' 6'" deep to 10' deep by increasing the distance between the ribs of the frame.

The said frame and compartments will be shaped in such a manner to be part of a system that attenuates acoustic energy laterally and focuses occupant generated acoustic energy to the floor, thus reducing and attenuating acoustic energy in the immediate vicinity of the said frame. Acoustic energy focusing will be accomplished by shaping the doors covering each said compartment to reflect acoustic energy to a focus point that will both retard sound propagation laterally to, adjacent occupants and will increase the intelligibility of speech between a caregiver and the occupant and conversely, from the occupant to the caregiver. The said doors may be shaped to follow a curve that continuously focuses acoustic energy as in the preferred embodiment, or in an alternative embodiment the said doors may be flat to create a series of surfaces each angled to result in reflecting acoustic energy to a similar point in space as the preferred embodiment.

REFERENCE NUMBERS IN THE DRAWINGS

Figure 1:
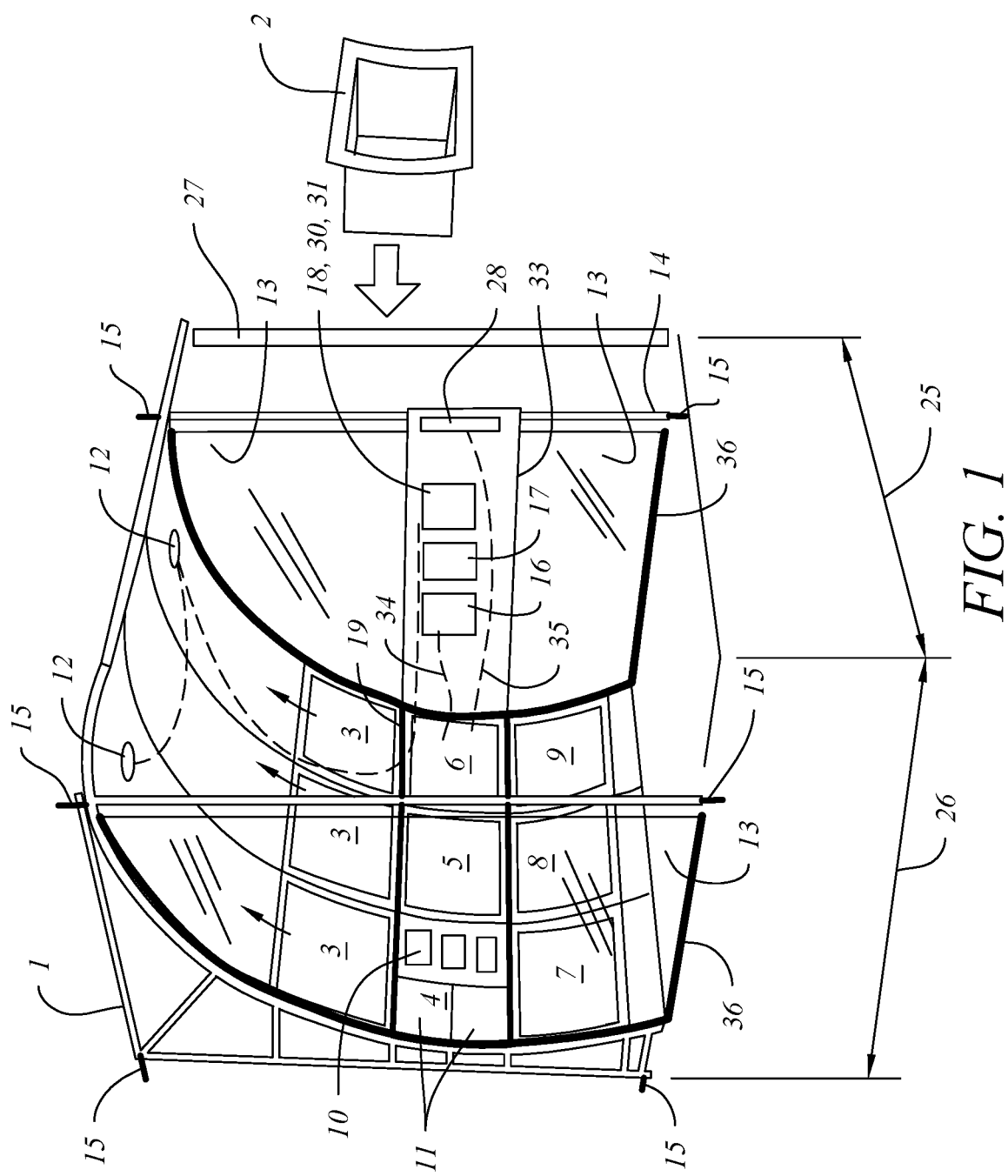
FIG. 1 is an oblique view of the entire device

1 Frame
2 Typical modular compartment made of highly cleanable/seamless easily cleanable material
3 Modular compartment slide-up doors for. EKG and medical equipment compartment
4 Modular compartment door for medical supplies and gloves
5 Modular compartment door for compartment medical supplies
6 Modular compartment door for compartment medical supplies
7 Modular compartment door for occupant belongings
8 Modular compartment door for waste 9 Modular compartment door for device electronics
10 gloves container
11 tilt-down medical supply storage
12 Lights controlled by 18, 30, 31
13 piezo electric glass switchable from clean to opaque for visual and acoustic privacy
14 Support pole
15 attachment to floor, ceiling and wall for stability
16 Outlets for 110 v, USB power
17 Pull-down occupant table
18 Control for lights
19 Infectious disease control surface
20 Occupant in reclining chair
21 Caregiver
22 Reflected sound waves
23 surface of frame reflecting sound
24 Floor, ceiling, wall of environment
25 Range of width of the device
26 Range of depth of the device
27 cubicle curtain and ceiling track which is designed to provide visual privacy
28 4-110 v, 4-USB power outlets
29 pivot in X and Y axis to adjust computer tablet 30,31 for occupant vision angle
30 metal security container for computer tablet 31 to protect against theft and damage
32 DC power for computer tablet 30,31 encased in 33
33 side panel for mounting of 16, 17, 18, 28, 29, 30, 31
34 AC/DC power from wall source to 16 encased in 33
35 AC/DC power from wall source to 28 encased in 33
36 metal support mullion to secure sidewall 13 to frame 1
37 support rib
38 horizontal struts
39 'L' brackets machine screwed (40) to 37 and 39
40 machine screws used to connect 37, 38 and 39
41 filler piece to adjust size

DETAILED DESCRIPTION OF THE INVENTION

FIG. 1 is an oblique view of the entire device assembly, the supporting frame 1, its connection to the wall, floor and ceiling 15, the modular compartments 3, 4,5,6,7,8,9; lift doors covering compartments 3. Compartments 3 are located to provide optimum height and size for services such as physiological monitors, nurse sharps container, supplies to be used in conjunction with the physiologic monitors, Pressurized medical gasses: oxygen, vacuum, medical air, extensible exam light; 110 v power for said devices. Compartments 3 all have lift doors that are either manual or motorized to provide safety and protection from infectious diseases. Compartment 4 contains sub-drawers 11 for common medical supplies: bandages, tape, scissors, a locked drawer for controlled medications, three sub drawers for three sizes of gloves 10. Compartments 5, 6 is for back-up medical supplies and future yet to be devised devices and has tilt-down hinged locked doors. Compartment 7 is for occupant personal belongings such as, clothing, computers, mobile devices and has 110 v and USB power within it. Compartment 8 is non-infectious waste and compartment 9 is for infectious waste. Both are protected from occupants by tilt down hinged doors. Piezo electric privacy glass on each side 13 of the frame 1, a typical modular easily cleanable compartment for housing supplies and equipment 2, vertical and lateral stability supports 14, lights 12, that are controlled via a touch-pad, or on a tilt out computer tablet 18, that also displays occupant distraction programs such as educational material or movies. As all contemporary tablets also have a self facing camera and networking capability built in, that same tablet could be used for communication to a translator or other medical providers 18, A pull-down table for occupant belongings such as beverages, mobile devices and small personal items such as keys, wallet 17, Power outlets (110v, USB), emergency call button, network connectors for staff devices 16, specially treated surfaces that are antimicrobial to avoid nosocomial infectious disease transfer to staff and occupants 19, may be achieved by multiple methods utilizing commercially available materials such as copper infused metals, laser etched patterns in dense plastic, near ultraviolet light shining on the surface and area that is high-touch 19, The width of the device is determined by the space required to position a recliner/exam chair and a caregiver in the proper position to conduct medical examinations or procedures which is a minimum of 5 feet to a maximum of 8 feet 25, the depth is determined by providing enough space for a recliner/exam chair to be fully extended horizontally and still have the cubicle curtain close to provide visual privacy to the occupant which is a range of between 7 feet 6 inches to 10 feet. The range of sizes is accomplished through a filler panel added to each side of the frame 41 to adapt to as-built sizes.

Figure 2:
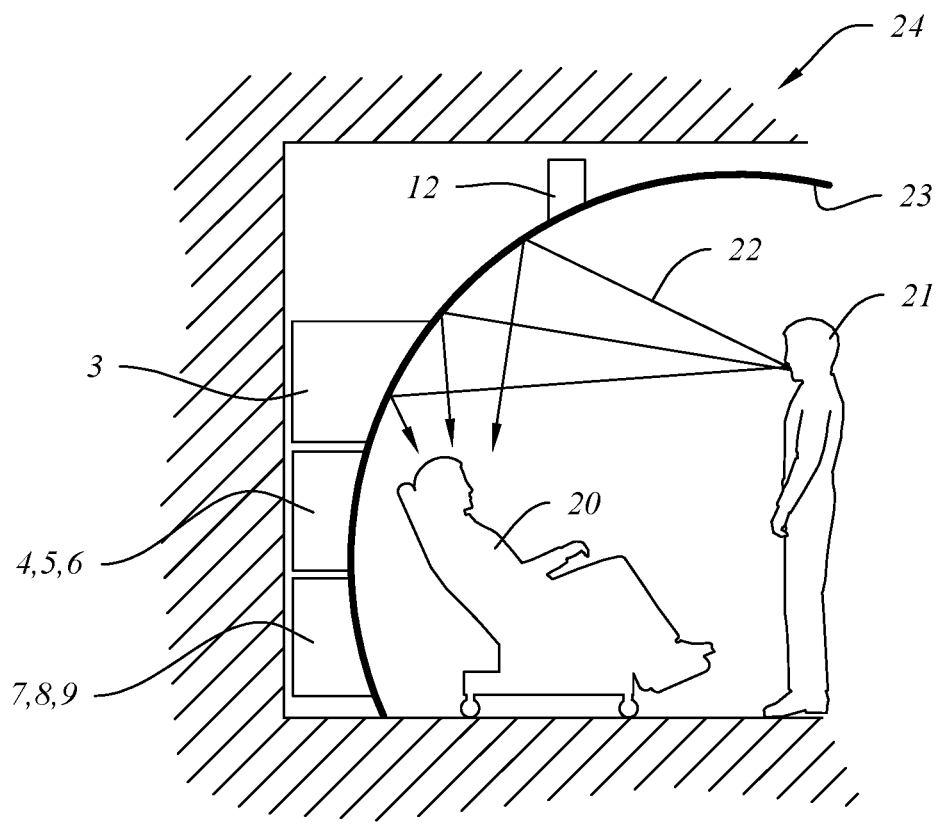
FIG. 2 is a side view of the device in the preferred configuration showing focused sound reflection from a caregiver to the surface of the frame to the seated occupant.

FIG. 2 depicts a side view of the occupant facing surface of the device (the support frame is omitted for clarity) 23, sound waves are shown reflecting from the caregiver 21, to the occupant 20, depicting that sound from the caregiver is effectively focused to the occupant to improve intelligibility and the wall, floor and ceiling are shown as item 24.

Figure 3:
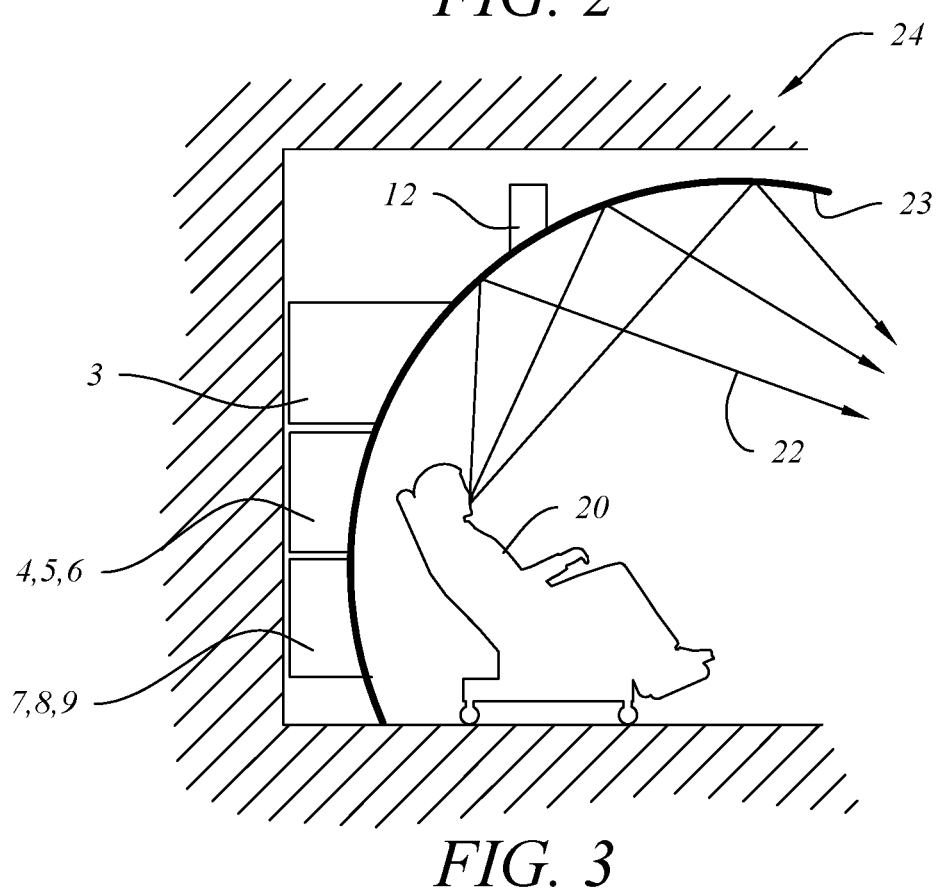
FIG. 3 shows a side view of the device in the preferred configuration as in FIG. 2 with reflected sound from the occupant focused to the floor outside the device.

FIG. 3. illustrates how sound from the occupant 20, is reflected towards the floor to attenuate the propagation of sound between occupants 22.

Figure 4:
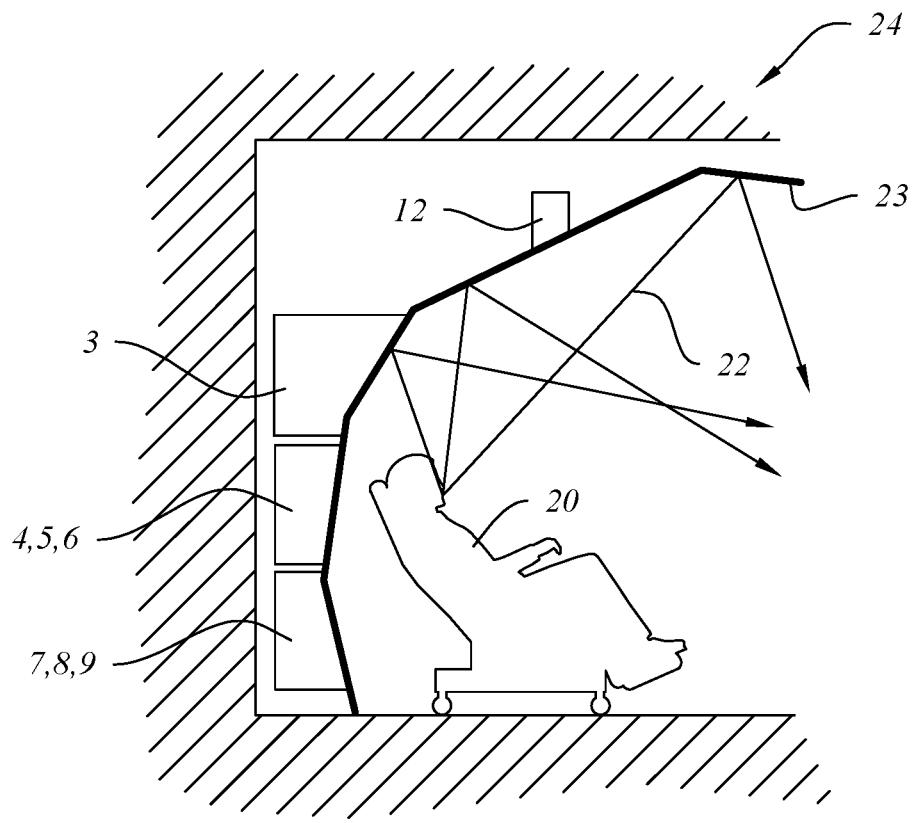
FIG. 4 is a side view of another alternative embodiment of FIG. 2
Figure 5:
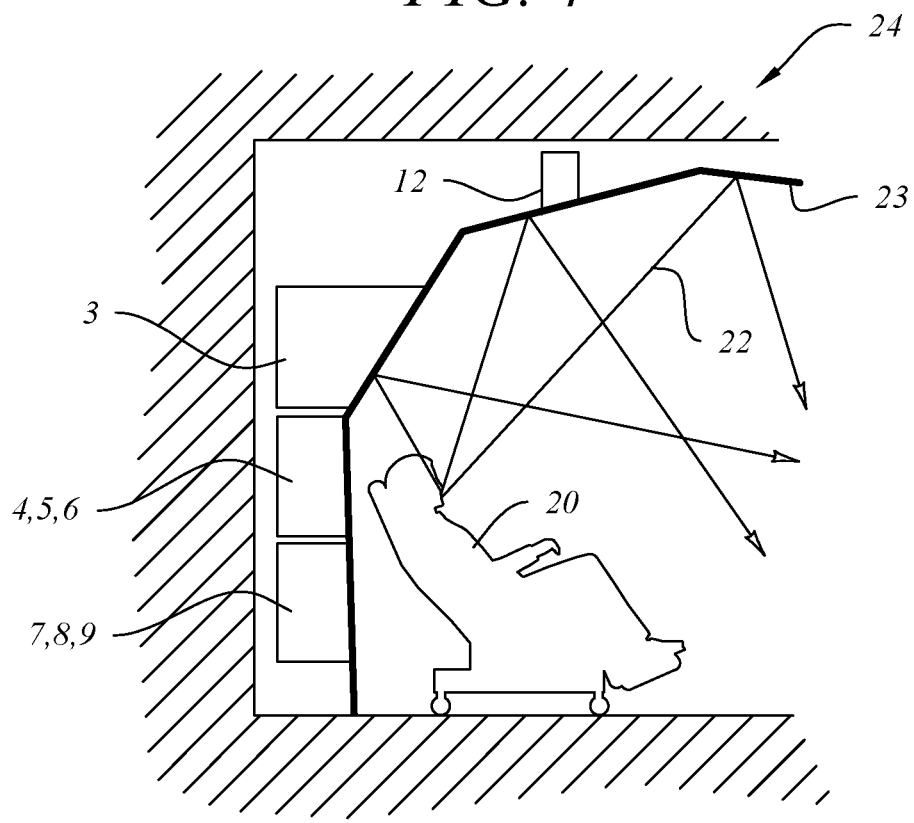
FIG. 5 is a side view of another alternative embodiment of FIG. 2
Figure 6:
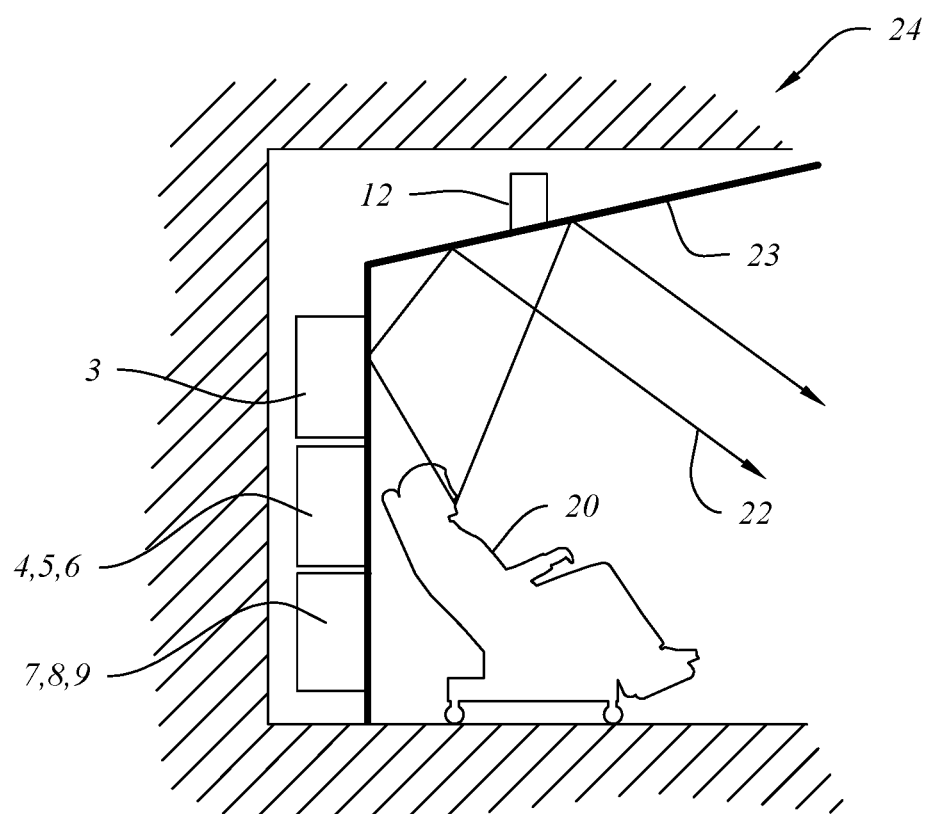
FIG. 6 is a side view of another alternative embodiment of FIG. 2

FIGS. 4, 5 and 6 are alternative embodiment examples of different methods of achieving the desirable reflection of acoustic energy 22, from the occupant 20.

Figure 7:
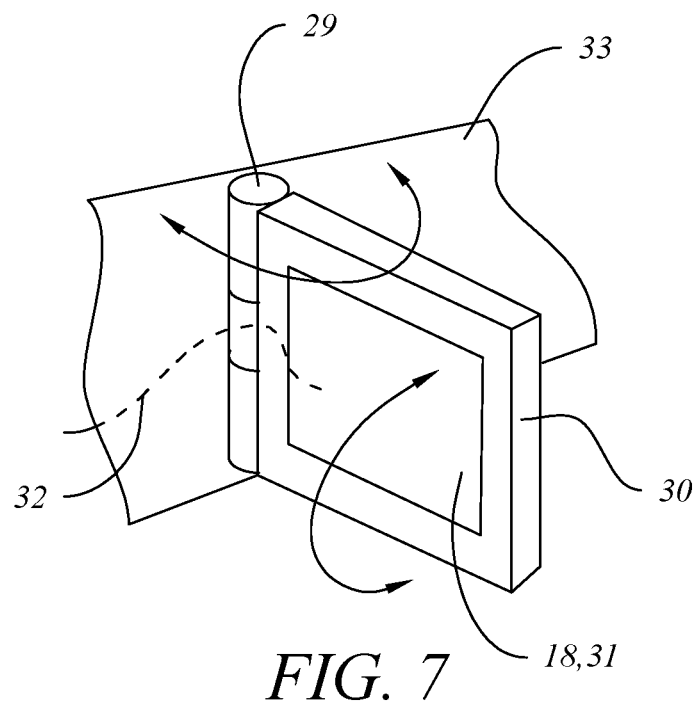
FIG. 7 is a partial oblique view of the sidewall illustrating the pivoting device used to secure the computer tablet to the frame.

FIG. 7. is a partial view of the sidewall 13 depicting a housing for a pivot-out computer tablet 18,30,31 that is capable of rotating in the 'X' and 'Y' directions to adjust the computer tablet 18,30,31 to an angle suitable to the occupant.

Figure 8:
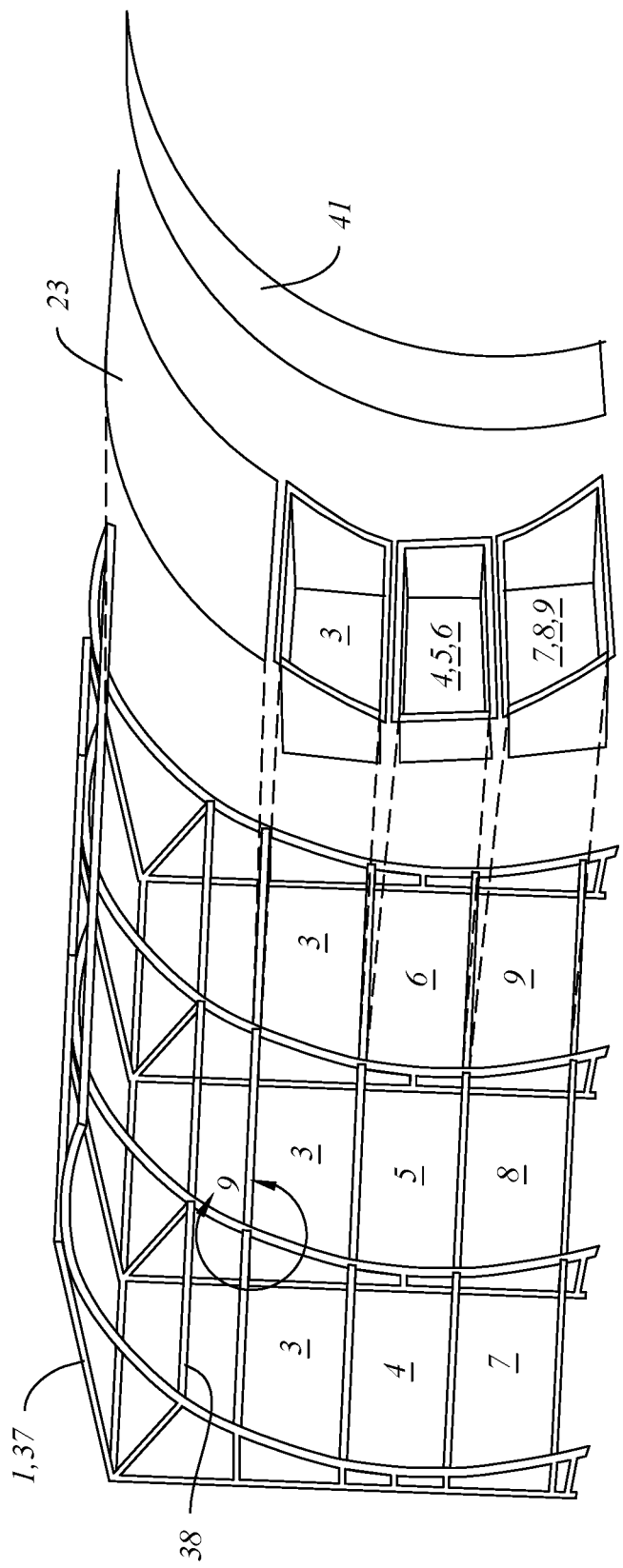
FIG. 8 is an oblique view of the structural support of the frame, the compartment configuration and shaping of frame surfaces and adaptation of the frame width to various sized environments.

FIG. 8. is an oblique angle view of frame 1, illustrating the basic structural system which is a series of ribs 37 separated by struts 38 which are connected by brackets 39 with machine screws 40. Filler panels 41 are used to facilitate the frames ability to adapt to fit various as-built widths in existing and new facilities. Modular compartments are inserted between the ribs to house various medical utilities and services along with occupant amenities as in FIG. 1.

Figure 9:
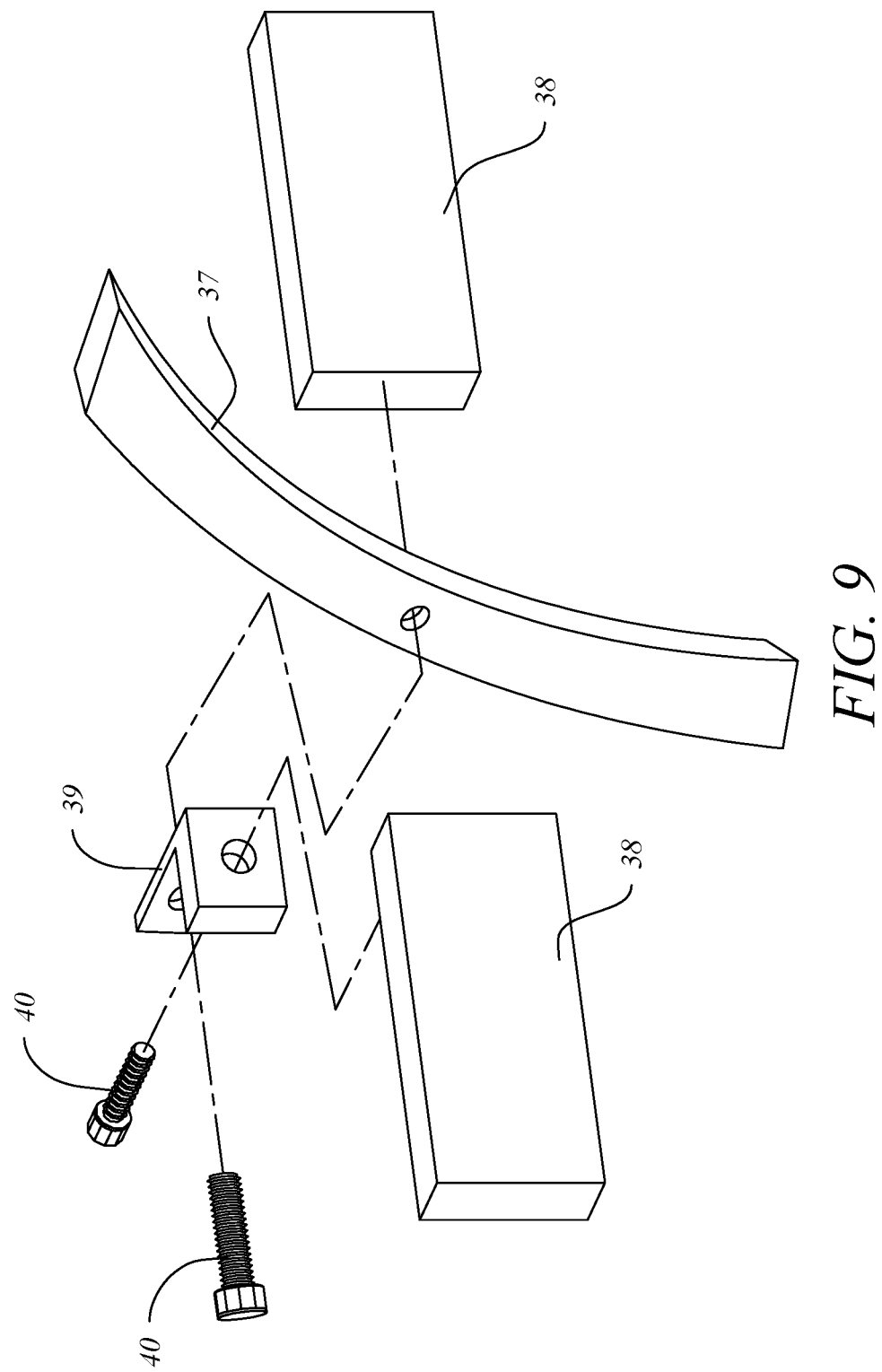
FIG. 9 is an oblique view of attaching the struts to the ribs of the frame which allows for disassembly and reassembly.

FIG. 9. is an exploded view of a typical connection at the intersection of the structural ribs and the struts which are joined together by an 'L' clip machine screwed together using 37,38,39 and 40.

Although the preceding description contains significant detail, it should not be construed as limiting the scope of the invention, but rather as providing illustrations of the preferred embodiments of the invention. As an example, acoustic energy features illustrated could take many different forms as in FIGS. 2, 3, 4,5 and 6. Alternative methods of attaching to the existing building and treatment platforms could take many different forms to accomplish the same purpose. The physical shape of the frame may vary to allow for adaption to various medical treatment platforms and construction materials. Such variations would not materially alter the nature of the invention. Thus, the scope of the invention should be fixed by the following claims rather than any specific example provided.

The invention claimed is:

1. A compact medical treatment, examination and waiting station disposed inside and attachable to a building structure of a hospital, emergency department, infusion service, outpatient clinic or industrial medicine site, said station comprising:
   a frame assembly further comprising a plurality of cooperatively assembled frame members and surfaces, poles, ribs and struts, which frame assembly is releasably attachable to a floor and wall and ceiling of the existing building structure and defines and provides structural support for a compact medical examination and treatment space having forwardly facing rear wall portions projecting overhead, said compact medical examination and treatment space being sufficient to receive a reclining examination chair for an occupant seeking medical treatment by an on-site medical caregiver within the space, and which frame assembly is selectively movable as an assembled unit from a first location to a second location or can be disassembled into components for relocation to and reassembly at the second location; and
   a plurality of modular compartments releasably inserted between the ribs and attachable to the frame assembly to form a part of the forwardly facing rear wall portions projecting overhead above the compact medical examination and treatment space for the reclining examination chair;
   wherein the frame assembly and modular compartments further comprise connection points for medical equipment and medical utilities at positions readily accessible for utilization by the on-site medical caregiver while treating the occupant seeking medical treatment within the compact medical examination and treatment space, and provide accessible storage space for medical supplies and for personal amenities of the occupant; and
   wherein the forwardly facing rear wall portions projecting overhead above the space for the reclining examination chair are configured and cooperate to selectively reflect, focus and attenuate acoustic energy in a desired direction within the compact medical examination and treatment space.

2. The compact medical treatment, examination and waiting station of claim 1 wherein medical equipment includes physiological monitoring equipment.

3. The compact medical treatment, examination and waiting station of claim 1 wherein the frame assembly and modular compartments comprise outlets for AC and DC electrical power and internet access.

4. The compact medical treatment, examination and waiting station of claim 1 wherein the medical utilities are selected from the group consisting of pressurized oxygen, suction, and medical air.

5. The compact medical treatment, examination and waiting station of claim 1 wherein at least one of the modular compartments further comprises a door selectively controlling access to at least one of the group consisting of medical utilities, medical equipment, medical supplies and medications.

6. The compact medical treatment, examination and waiting station of claim 1 further comprising at least one sidewall divider, wherein the at least one sidewall divider supports controls for medical equipment and medical utilities selected from the group consisting of lights, nurse call alerts, 110-volt power, direct current power, USB power, television and internet.

7. The compact medical treatment, examination and waiting station of claim 6 wherein the at least one sidewall divider comprises piezo-electric glass.

8. The compact medical treatment, examination and waiting station of claim 6, wherein the at least one sidewall divider further comprises a pull-down storage shelf.

9. The compact medical treatment, examination and waiting station of claim 1 wherein the modular compartments comprise a combination of lift doors and tilt-down hinged doors.

10. The compact medical treatment, examination and waiting station of claim 1 wherein the medical equipment comprises I.V. pumps and computer terminal support arms.

11. The compact medical treatment, examination and waiting station of claim 1 wherein the frame assembly can be assembled to define said compact medical treatment and examination space with dimensions ranging from 5 feet wide and 7 feet 6 inches deep to 8 feet wide and 10 feet deep.

12. The compact medical treatment, examination and waiting station of claim 11 wherein the frame assembly further comprises at least one forwardly facing, curved filler panel projecting overhead for use in adapting the frame assembly to fit various as-built widths in new or existing facilities.

13. The compact medical treatment, examination and waiting station of claim 1 in combination with said reclining examination chair disposed within the compact medical examination and treatment space in which said occupant can recline and await or receive medical examination and treatment inside the compact medical examination and treatment space.

14. The compact medical treatment, examination and waiting station of claim 1 wherein the ribs and struts of the frame assembly are selectively engageable and intersect and cooperate to support the modular compartments to achieve desired dimensions, shape and acoustic properties for said compact medical treatment, examination and waiting station.

15. The compact medical treatment, examination and waiting station of claim 14 wherein the modular compartments comprise forwardly facing doors and drawers that cooperate to create a series of surfaces angled to reflect acoustic energy to a similar point within said compact medical examination and treatment space.

16. The compact medical treatment, examination and waiting station of claim 1 comprising readily cleanable, smooth and durable materials selected from the group consisting of metal, wood product and plastic.

17. The compact medical treatment, examination and waiting station of claim 1 further comprising a modular compartment for temporary storage of waste.

* * * * *

UNITED STATES PATENT AND TRADEMARK OFFICE
CERTIFICATE OF CORRECTION

| | | |
|---|---|---|
| PATENT NO. | : 11,369,536 B2 | |
| APPLICATION NO. | : 17/153531 | |
| DATED | : June 28, 2022 | |
| INVENTOR(S) | : James Albert Lennon | |

It is certified that error appears in the above-identified patent and that said Letters Patent is hereby corrected as shown below:

In the Claims

Column 7, Line 6 in Claim 1, "of a hospital" should read -- of an existing hospital --.

Column 7, Lines 7-8 in Claim 1, "said station comprising" should read -- said compact medical treatment, examination and waiting station --.

Column 7, Lines 12-13 in Claim 1, "ceiling of the existing building" should read -- ceiling of the building --.

Column 7, Line 20 in Claim 1, "within the space" should read -- within the compact medical examination and treatment space --.

Column 7, Line 20 in Claim 1, "and which frame assembly" should read -- and wherein the frame assembly --.

Column 7, Line 41 in Claim 1, "above the space" should read -- above the compact medical examination and treatment space --.

Column 7, Line 47 in Claim 2, "wherein medical equipment" should read -- wherein the medical equipment --.

Column 8, Lines 24-25 in Claim 11, "compact medical treatment and examination space" should read -- compact medical examination and treatment space --.

Signed and Sealed this
Eleventh Day of June, 2024

*Katherine Kelly Vidal*

Katherine Kelly Vidal
*Director of the United States Patent and Trademark Office*